United States Patent [19]
Southan et al.

[11] Patent Number: 5,952,385
[45] Date of Patent: Sep. 14, 1999

[54] MERCAPTO DERIVATIVES AS INHIBITORS OF NITRIC OXIDE SYNTHASE

[75] Inventors: Garry J. Southan; Andrew L. Salzman; Csaba Szabó, all of Cincinnati, Ohio

[73] Assignee: Children's Hospital Medical Center, Cincinnati, Ohio

[21] Appl. No.: 08/889,379

[22] Filed: Jul. 8, 1997

Related U.S. Application Data

[62] Division of application No. 08/410,312, Mar. 24, 1995, Pat. No. 5,674,907.

[51] Int. Cl.$^6$ .......................... A61K 31/155; A61K 31/55; A61K 31/54; A61K 31/425
[52] U.S. Cl. ...................... 514/634; 514/211; 514/224.2; 514/368; 514/665
[58] Field of Search ..................................... 514/634, 211, 514/224.2, 368, 665

[56] References Cited

FOREIGN PATENT DOCUMENTS

| 547558 | 6/1993 | European Pat. Off. . |
| 1400319 | 7/1975 | United Kingdom . |
| 12165 | 6/1994 | WIPO . |

OTHER PUBLICATIONS

Khym et al., Ion Exchange Studies of Transguanylation Reactions. I. Rearrangement of S,2–Aminoethylisothiourea . . . Aminothiazoline *Journal of the American Chemical Society*, vol. 79, pp. 5663–5666, Nov. 5, 1957.

Doherty et al., "Synthesis of Aminoalkylisothiuronium Salts and their Conversion to Mercaptoalkylguanidines and Thiazolines", *Journal of the American Chemical Society*, vol. 79, pp. 5667–5671, Nov. 5, 1957..

Khym et al., "Ion Exchange Studies of Transguanylation Reactions. II. . . . and 2–Aminothiazolines or Penthiazolines", *Journal of the American Chemical Society*, vol. 80, pp. 3342–3349, Jul. 5, 1958.

Doherty et al., "Synthesis of D– and L–2–Aminobutylisothiourea Dihydrobromide Isomers and their Conversion to Guanidothiols, Disulphides, and Thiazolines", *Journal of Organic Chemistry*, vol. 28, pp. 1339–1342, 1963.

Szabó et al., "Beneficial effects and improved survival in rodent models . . . nitric oxide synthase", *Pharmacology*, vol. 91, pp. 12472–12476, Dec. 1994.

Southan et al., "Isothioureas: potent inhibitors of nitric oxide synthases . . . selectivity", *British Journal of Pharmacology*, vol. 114, pp. 510–516, 1995.

Wu et al., "Aminoguanidine attenuates the delayed circulatory failure and . . . shock", *British Journal of Pharmacology*, vol. 113, pp. 001–007, Paper No. 78594, 1994.

*Chemical Abstracts*, vol. 82, 1975, p. 12, #164694y, Tumor rejection in experimental animals treated with radioprotective thiols.

*Cancer Research* 35. 429–437., Feb. 1975, *Tumor Rejection in Experimental Animals Treated with Radioprotective Thiols*.

*Primary Examiner*—Theodore J. Criares
*Attorney, Agent, or Firm*—Wood, Herron & Evans, L.L.P.

[57] ABSTRACT

This invention is directed to a pharmacologically acceptable composition for inhibiting nitric oxide synthase in a mammal, which includes a mercapto derivative and a pharmaceutically acceptable carrier. The invention also concerns a method of inhibiting nitric oxide synthase, selectively inhibiting the inducible isoform of nitric oxide synthase, and treating various conditions where there is an advantage in inhibiting nitric oxide biosynthesis. The method includes the step of administering to a mammal a mercapto derivative in pure form or in a pharmaceutically acceptable carrier.

23 Claims, 3 Drawing Sheets

MERCAPTO DERIVATIVES AS INHIBITORS OF NITRIC OXIDE SYNTHASE

This is a division of application Ser. No. 08/410,312, filed Mar. 24, 1995, now U.S. Pat. 5,674,907.

BACKGROUND OF THE INVENTION

The present invention relates to the use of mercapto derivatives as inhibitors of nitric oxide synthase (NOS).

The free radical nitric oxide (NO) is synthesized from the guanidino group of L-arginine by a family of enzymes termed nitric oxide synthase (NOS). The brain isoform (bNOS) is constitutively present in the neural tissue and NO is released as a neurotransmitter by activation of various (e.g. NMDA-type) receptors. NO in the central nervous system plays an important role in the genesis of memory.

The continuous release of NO from the constitutive endothelial isoform of NOS (ecNOS) keeps the vasculature in a continuous state of active vasodilatation and reduces the adhesion of platelets and polymorphonuclear granulocytes (PMNs) to the endothelial surface. The biological activity of NO from the ecNOS was originally described as endothelium-derived relaxing factor (EDRF). The release of EDRF in vivo and in vitro is stimulated by shear stress and various hormones and autocoids such as acetylcholine, bradykinin, substance P. vasopressin, noradrenaline, histamine or platelet-activating factor.

The inducible isoform of NOS (iNOS) is expressed in response to immunological stimuli in multiple cell types including macrophages, vascular smooth muscle cells and epithelial cells, and produces large amounts of NO (nanomoles of NO rather than picomoles of NO derived by the ecNOS or bNOS). NO in high local concentrations can act as a cytostatic and cytotoxic molecule acting against fungal, bacterial, helminthic and protozoal antigens as well as tumor cells. A number of pro-inflammatory cytokines and endotoxin (bacterial lipopolysaccharide, LPS) also induce the expression of iNOS in a number of other cells, including fibroblasts, glial cells, cardiac myocytes as well as vascular and non-vascular smooth muscle cells.

There is now substantial evidence that iNOS plays an important role in the pathogenesis of a variety of diseases. Circulatory shock of various etiologies is associated with profound changes in the body's NO homeostasis. In animal models of endotoxic shock, endotoxin produces an acute release of NO from constitutive isoform of nitric oxide synthase in the early phase, which is followed by induction of iNOS. In addition, it is now thought that excess NO production may be involved in a number of conditions, including conditions that involve systemic hypotension such as septic (toxic) shock and therapy with certain cytokines. Therefore, it is desirable to inhibit nitric oxide synthase. Furthermore, because of the potentially serious consequences of over-inhibition of the constitutive NOS enzyme, it is preferred to selectively inhibit the inducible isoform. Over-inhibition of the constitutive isoform may lead to hypotension, thrombosis, central nervous system toxicity and tissue damage.

Various nitric oxides synthase inhibitors have been proposed for therapeutic use. For example, NG-methyl-L-arginine (L-NMA) and NG-nitro-L-arginine methyl ester (L-NAME) have been suggested, however, they are generally nonselective in that they inhibit both the constitutive and the inducible NOS isoforms to a similar extent. Other NOS inhibitors proposed for therapeutic use include isothiourea derivatives and aminoguanidine. In in vitro and in vivo tests, isothioureas have been shown to inhibit NOS activity, and a few specific compounds within the class of isothioureas have been shown to be relatively selective inhibitors of iNOS activity (see, for example, Garry J. Southan et al., "Isothioureas: Potent Inhibitors of Nitric Oxide Synthases with Variable Isoform Selectivity", *British Journal of Pharmacology*, Vol. 114, pp. 510–516, 1995; Csaba Szabó et al., "Beneficial Effects and Improved Survival in Rodent Models of Septic Shock with S-methylisothiourea Sulfate, a Potent and Selective Inhibitor of Inducible Nitric Oxide Synthase", *Pharmacology*, Vol. 91, pp. 12472–12476 (December 1994); and PCT Application No. WO 94/12165). Aminoguanidine also has been found to selectively inhibit the inducible isoform of nitric oxide synthase in various in vitro and in vivo models (see, for example, Chin-Chen Wu et al., "Aminoguanidine Attenuates the Delayed Circulatory Failure and Improves Survival in Rodent Models of Endotoxic Shock", *British Journal of Pharmacology*, Vol. 113, pp. 001–007, Paper No. 78594 (1995); and European Patent Application 0 547 558 A1).

Although the nitric oxide synthase inhibitors discussed above may prove to have therapeutic use, it is important to identify additional compounds which inhibit nitric oxide synthase. It also is desirable to identify additional compounds which selectively inhibit the inducible isoform of the NOS enzyme. Because excess nitric oxide production plays such a role in a number of different disorders and conditions, such as systemic hypotension, septic shock and cytokine therapy, for example, it is extremely important to identify additional compounds capable of inhibiting, and even selectively inhibiting, nitric oxide synthase. This is especially true given that such additional compounds may prove to have fewer side effects and greater selectivity in inhibiting the inducible nitric oxide synthase enzymes.

SUMMARY OF THE INVENTION

This invention is directed to a pharmacologically acceptable composition for inhibiting nitric oxide synthase in a mammal. The composition includes a mercapto derivative and a pharmaceutically acceptable carrier, with the mercapto derivative present in the composition in an effective amount to inhibit nitric oxide synthase in the mammal.

The invention also is directed to a method of inhibiting nitric oxide synthase in a mammal, which includes the step of administering to the mammal a mercapto derivative in a pure form or in a pharmaceutically acceptable carrier.

The mercapto derivative of the composition and method is defined by the formula:

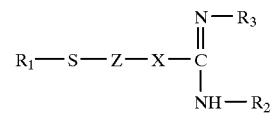

or a salt thereof, wherein

R$_1$ is H, alkyl, alkenyl, phenyl, alkylene, alkenylene, or phenylalkylene or a substituted derivative thereof;

When R$_1$ is alkylene or alkenylene, R$_1$ optionally may be joined to either of the amidino Ns, to Z or to X of the above formula to form a 5-, 6- or 7- membered heterocyclic ring, with the proviso that, when R$_1$ is attached to Z, Z is alkylene or alkenylene or a substituted derivative thereof, and, when R$_1$ is attached to X, X is either CR$_5$ or N;

R$_2$ and R$_3$ are independently H, lower alkyl, alkenyl, alkylene, alkenylene, amino, phenyl or phenylalkylene, or a substituted derivative thereof;

When $R_2$ is alkylene or alkenylene, $R_2$ optionally may be joined to the imino N of the above formula to form a 5- or 6- membered heterocyclic ring;

Z is an alkylene, alkenylene, cycloalkylene or cycloalkenylene, or a substituted derivative thereof;

When $R_2$ or $R_3$ is alkylene or alkenylene, $R_2$ or $R_3$ optionally may be joined to Z to form a 5- or 6- membered heterocyclic ring including N, C and not more than one atom of 0 or S, with the proviso that Z is an alkylene or alkenylene, said heterocyclic ring optionally being substituted with a lower alkyl, alkoxy, halogen, hydroxy or amino;

X is N, $NR_4$, O, $CR_5$ or $CR_4 R_5$;

$R_4$ is independently H, alkyl, alkylene, alkenylene, thioalkylene or thioesteralkylene;

$R_5$ is independently H, alkyl, alkylene, alkenylene, thioalkylene, thioesteralkylene, amino or carboxyl;

When $R_4$ is alkylene, alkenylene, thioalkylene, or thioesteralkylene, $R_4$ optionally may be joined to $R_2$ or $R_3$ to form a 5- or 6- membered heterocyclic ring including N, C and not more than one atom of O or S, with the proviso that $R_2$ or $R_3$ is alkylene, alkenylene, amino, phenyl, phenylalkylene, or a substituted derivative thereof wherein the substituted derivative is lower alkyl or halogen.

DETAILED DESCRIPTION OF THE INVENTION

Figure 1:
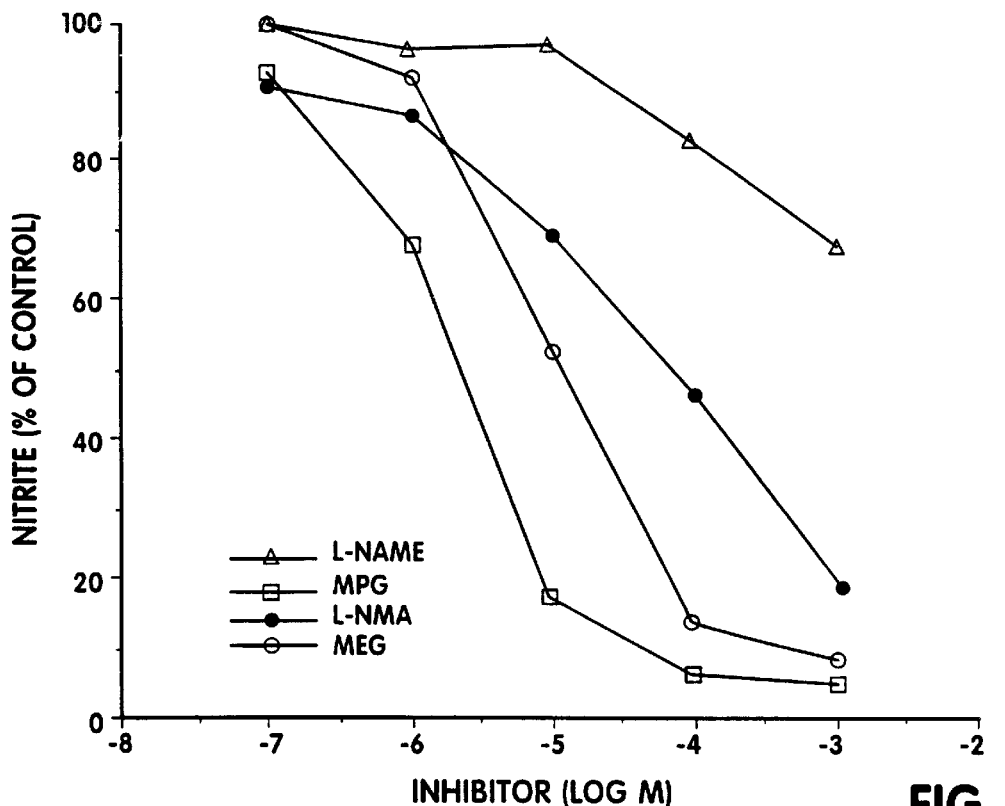
FIG. 1 is a graph of the effect of mercaptoethylguanidine (MEG), mercaptopropylguanidine (MPG), NG-methyl-L-arginine (L-NMA) and NG-nitro-L-arginine methyl ester (L-NAME) on nitrite production by immunostimulated J774 macrophages (N=3–6)

This invention is directed to a pharmacologically acceptable composition for inhibiting nitric oxide synthase in a mammal. The composition includes a mercapto derivative and a pharmaceutically acceptable carrier, with the mercapto derivative present in the composition in an effective amount to inhibit nitric oxide synthase in the mammal. The invention also is directed to a method of inhibiting nitric oxide synthase in a mammal, which includes the step of administering to the mammal a mercapto derivative in pure form or in a pharmaceutically acceptable carrier.

Suitable mercapto derivatives for use in the composition or method may be made according to the methods of synthesis taught in the following articles which are incorporated herein in their entirety by reference:

(1) Joseph X. Khym et al., "Ion Exchange Studies of Transguanylation Reactions. I. Rearrangement of S,2-Aminoethylisothiourea to 2-Mercaptoethylguanidine and 2-Aminothiazoline", *Journal of the American Chemical Society*, Vol. 79, pp 5663–5666, Nov. 5, 1957;

(2) David G. Doherty, et al., "Synthesis of Aminoalkylisothiuronium Salts and their Conversion to Mercaptoalkylguanidines and Thiazolines", *Journal of the American Chemical Society*, Vol. 79, pp 5667–5671, Nov. 5, 1957;

(3) Joseph H. Khym, et al., "Ion Exchange Studies of Transguanylation Reactions. II. Rearrangement of 3-Aminopropylisothiourea and N-Substituted Aminoethyl- and Aminopropylisothioureas to Mercaptoalkylguanidines and 2-Aminothiazolines or Penthiazolines", *Journal of the American Chemical Society*, Vol. 80, pp 3342–3349, Jul. 5, 1958;

(4) Doherty et al. "Synthesis of D- and L-2-Aminobutylisothiourea Dihydrobromide Isomers and their Conversion to Guanidothiols, Disulphides, and Thiazolines", *Journal of Organic Chemistry*, Vol. 28, pp 1339–1342, 1963.

Suitable mercapto derivatives also may be made according to the examples provided at the end of this detailed description of the invention.

The mercapto derivative of the composition and method is defined by the formula:

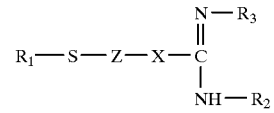

or a salt thereof, wherein $R_1$ is H, alkyl, alkenyl, phenyl, alkylene, alkenylene, or phenylalkylene or a substituted derivative thereof;

When $R_1$ is alkylene or alkenylene, $R_1$ optionally may be joined to either of the amidino Ns, to Z or to X of the above formula to form a 5-, 6- or 7- membered heterocyclic ring, with the proviso that when $R_1$ is attached to Z, Z is alkylene or alkenylene or a substituted derivative thereof, and, when $R_1$ is attached to X, X is either $CR_5$ or N;

$R_2$ and $R_3$ are independently H, lower alkyl, alkenyl, alkylene, alkenylene, amino, phenyl or phenylalkylene, or a substituted derivative thereof;

When $R_2$ is alkylene or alkenylene, $R_2$ optionally may be joined to the imino N of the above formula to form a 5- or 6- membered heterocyclic ring;

Z is an alkylene, alkenylene, cycloalkylene or cycloalkenylene, or a substituted derivative thereof;

When $R_2$ or $R_3$ is alkylene or alkenylene, $R_2$ or $R_3$ optionally may be joined to Z to form a 5- or 6- membered heterocyclic ring including N, C and not more than one atom of 0 or S, with the proviso that Z is an alkylene or alkenylene, said heterocyclic ring optionally being substituted with a lower alkyl, alkoxy, halogen, hydroxy or amino;

X is N, $NR_4$, O, $CR_5$ or $CR_4 R_5$;

$R_4$ is independently H, alkyl, alkylene, alkenylene, thioalkylene.or thioesteralkylene;

$R_5$ is independently H, alkyl, alkylene, alkenylene, thioalkylene, thioesteralkylene, amino or carboxyl;

When $R_4$ is alkylene, alkenylene, thioalkylene, or thioesteralkylene, $R_4$ optionally may be joined to $R_2$ or $R_3$ to form a 5- or 6- membered heterocyclic ring including N, C and not more than one atom of O or S, with the proviso that $R_2$ or $R_3$ is alkylene, alkenylene, amino, phenyl, phenylalkylene, or a substituted derivative thereof wherein the substituted derivative is lower alkyl or halogen.

As used herein, the term "salt" refers to any addition salt derived from any pharmaceutically acceptable organic or inorganic acid. Examples of suitable acids include hydrochloric, hydrobromic, sulfuric, nitric, perchloric, fumaric, maleic, phosphoric, glycolic, lactic, salicylic, succinic, toluene p sulfonic, tartaric, acetic, citric, methanesulfonic, formic, benzoic, malonic, naphthalene-2-sulfonic and benzenesulphonic acids. Additionally, as used herein, any alkyl or alkylene may be straight chain, branched or cyclic, and "halogen" includes bromine, chlorine, fluorine and iodine.

As mentioned above, $R_1$ is H, alkyl, alkenyl, phenyl, alkylene, alkenylene or phenylalkylene, or a substituted derivative thereof. If desired, this $R_1$ derivative may be substituted with one or more alkoxy, halogen, hydroxy, amino or nitro groups. Additionally, as noted above, $R_2$ and $R_3$ are independently H, lower alkyl, alkenyl, alkylene, alkenylene, amino, phenyl or phenylalkylene, or a substituted derivative thereof. If desired, the $R_2$ or $R_3$ derivative may be substituted with a lower alkyl or halogen.

If the $R_4$ or $R_5$ substituent is thioalkylene, the thioalkylene has a formula $[-(CH_2)_n-SH]$ where n is 1 to 4. If $R_4$ or $R_5$ is thioesteralkylene, the thioesteralkylene may have the formula $[-(CH_2)_n-S-R_6]$ where $R_6$ is a lower alkyl and n is 1 to 4.

The Z substituent of the mercapto derivative is an alkylene, alkenlyene, cycloalkyene or cycloalkenlyene, or a substituted derivative thereof. When such a substituted derivative is employed, the substituent may include an alkoxy, halogen, hydroxy, amino or nitro group.

A preferred subgroup of the mercapto derivative includes mercapto derivatives where: $R_1$ is H or lower alkyl; $R_2$ is H; $R_3$ is H; X is $NR_4$; $R_4$ is H, methyl or ethyl, and Z is alkylene. A few nonlimiting examples include S-methyl-mercaptoethylguanidine and S-methyl-mercaptopropylguanidine. Another preferred subgroup of mercapto derivatives is formed wherein: $R_1$ is H; $R_2$ is H; $R_3$ is H; X is $NR_4$; $R_4$ is H; and Z is a $C_{1-6}$ alkylene. Nonlimiting examples include mercaptoethylguanidine and mercaptopropylguanidine.

The mercapto derivative, in pure form or in a pharmaceutically acceptable carrier, will find benefit in treating conditions and disorders where there is an advantage in inhibiting the nitric oxide synthase enzyme and selectively inhibiting the inducible isoform. For example, the mercapto derivative may be used to treat a circulatory shock including its various aspects such as vascular and myocardial dysfunction, metabolic failure including the inhibition of mitochondrial enzymes and cytochrome P450-mediated drug metabolism, and multiple organ dysfunction syndrome including adult respiratory distress syndrome. Circulatory shock may be a result of gram-negative and gram positive sepsis, trauma, hemorrhage, burn injury, anaphylaxis, cytokine immunotherapy, liver failure, kidney failure or systemic inflammatory response syndrome. Mercapto derivatives also may be beneficial for patients receiving therapy with cytokines such as TNF, IL-1 and IL-2 or therapy with cytokine-inducing agents, or an adjuvant to short term immunosuppression in transplant therapy. In additional mercapto derivatives may be useful to inhibit NO synthesis in patients suffering from inflammatory conditions in which an excess of NO contributes to the pathophysiology of the condition, such as adult respiratory distress syndrome (ARDS) and myocarditis, for example.

There is also evidence that an NO synthase enzyme may be involved in the pathophysiology of autoimmune and/or inflammatory conditions such as arthritis, rheumatoid arthritis and systemic lupus erythematosus (SLE) and in insulin-dependent diabetes mellitus, and therefore, mercapto derivatives may prove helpful in treating these conditions.

Furthermore, it is now clear that there are a number of additional inflammatory and noninflammatory diseases that are associated with NO overproduction. Examples of such physiological disorders include: inflammatory bowel diseases such as ileitis, ulcerative colitis and Crohn's disease; inflammatory lung disorders such as asthma and chronic obstructive airway disease; inflammatory disorders of the eye including corneal dystrophy, trachoma, onchocerciasis, uveitis, sympathetic ophthalmitis and endophthalmitis; chronic inflammatory disorders of the bum including periodontitis; chronic inflammatory disorders of the joints including arthritis and osteoarthritis, tuberculosis, leprosy, glomerulonephritis sarcoid, and nephrosis; disorders of the skin including sclerodermatitis, psoriasis and eczema; inflammatory diseases of the central nervous system, including chronic demyelinating diseases such as multiple sclerosis, dementia including AIDS-related neurodegeneration and Alzheimer's disease, encephalomyelitis and viral or autoimmune encephalitis; autoimmune diseases including immune-complex vasculitis, systemic lupus and erythematodes; and disease of the heart including ischemic heart disease and cardiomyopathy. Additional diseases may benefit from the use of mercapto derivatives include adrenal insufficiency; hypercholesterolemia; atherosclerosis; bone disease associated with increased bone resorption, e.g., osteoporosis, pre-eclampsia, eclampsia, uremic complications; chronic liver failure, noninflammatory diseases of the central nervous system (CNS) including stroke and cerebral ischemia; and various forms of cancer.

Pharmaceutical formulations of the mercapto derivative may include those suitable for oral, rectal, nasal, topical (including buccal and sub-lingual), vaginal or parenteral (including intramuscular, sub-cutaneous and intravenous) administration, or for administration by inhalation or insufflation. The formulations may, where appropriate, be conveniently presented in discrete dosage units and may be prepared by any of the methods well known in the art of pharmacy. All methods include the steps of bringing into association the active compound with liquid carriers or finely divided solid carriers or both and then, if necessary, shaping the product into the desired formulation.

Pharmaceutical formulations suitable for oral administration may conveniently be presented: as discrete units, such as capsules, cachets or tablets, each containing a predetermined amount of the active ingredient; as a powder or granules; or as a solution, a suspension or as an emulsion. The active ingredient may also be presented as a bolus electuary or paste, and be in a pure form, i.e., without a carrier. Tablets and capsules for oral administration may contain conventional excipients such as binding agents, fillers, lubricants, disintegrant or wetting agents. A tablet may be made by compression or molding, optionally with one or more accessory ingredients. Compressed tablets may be prepared by compressing in a suitable machine the active ingredients in a free-flowing form such as a powder or granules, optionally mixed with a binder, lubricant, inert diluent, lubricating, surface active or dispersing agent.

Molded tablets may be made by molding in a suitable machine a mixture of the powdered compound moistened with an inert liquid diluent. The tablets may be coated according to methods well known in the art. Oral fluid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservatives. The tablets may optionally be formulated so as to provide slow or controlled release of the active ingredient therein.

Formulations for parenteral administration include: aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit dose or multi-dose containers, for example sealed ampoules and vials, and may be stored in a freeze-dried (lyophilized) condition requiring only the addition of the sterile liquid carrier, for example, saline, water-for-injection, immediately prior to use. Alternatively, the formulations may be presented for continuous infusion. Extemporaneous injection solutions and suspensions may be prepared from sterile powders, granules and tablets of the kind previously described.

Formulations for rectal administration may be presented as a suppository with the usual carriers such as cocoa butter or polyethylene glycol. Formulations for topical administration in the mouth, for example buccally or sublingually, include lozenges, comprising the active ingredient in a flavored base such as sucrose and acacia or tragacanth, and pastilles comprising the active ingredient in a basis such as gelatin and glycerin or sucrose and acacia. For intra-nasal administration the compounds of the invention may be used as a liquid spray or dispersible powder or in the form of drops. Drops may be formulated with an aqueous or non-aqueous base also comprising one or more dispersing agents, solubilizing agents or suspending agents. Liquid sprays are conveniently delivered from pressurized packs.

For administration by inhalation the compounds according to the invention are conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount.

Alternatively, for administration by inhalation or insufflation, the compounds according to the invention may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

When desired the above described formulations, adapted to give sustained release of the active ingredient, may be employed. The pharmaceutical compositions according to the invention may also contain other active ingredients such as antimicrobial agents, immunosuppressants or preservatives.

The compounds of the invention may also be used in combination with other therapeutic agents for example anti-inflammatory agents, particularly non-steroidal anti-inflammatory drugs (NSAIDs) vasodilator prostaglandins including prostacyclin and prostaglandin $E_1$, cancer chemotherapeutic agents including cisplatin, NO donors or NO inhalation therapy, or PAF - receptor antagonists.

It should be understood that in addition to the ingredients particularly mentioned above, the formulations of this invention may include other agents conventional in the art having regard to the type of formulation in question, for example those suitable for oral administration may include flavoring agents.

Preferred unit dosage formulations are those containing an effective dose, as recited below, or an appropriate fraction thereof, of the active ingredient.

For each of the aforementioned conditions, the mercapto derivative may be administered orally or via injection at a dose of from 0.1 to 250 mg/kg per day. The dose range for adult humans is generally from 5 mg to 17.5 g/day, preferably 5 mg to 10 g/day and most preferably 100 mg to 3 g/day. Tablets or other forms of presentation provided in discrete units may conveniently contain an amount which is effective at such dosage or as a multiple of the same; for instance, units containing 5 mg to 500 mg, usually around 100 mg to 500 mg.

The pharmaceutical composition preferably is administered orally or by injection (intravenous or subcutaneous), and the precise amount administered to a patient will be the responsibility of the attendant physician. However, the dose employed will depend upon a number of factors, including the age and sex of the patient, the precise disorder being treated, and its severity. Also the route of administration may vary depending upon the condition and its severity.

The following Examples are provided by way of illustration, and are not intended to limit the scope of the invention.

EXAMPLE 1

This example illustrates the effect of selected mercapto derivatives on endotoxin-induced nitrite formation in J774.2 macrophages and on IL-1 gamma-interferon induced nitrite formation in cultured rat aortic smooth muscle cells. J774 macrophage cell lines were obtained from ATCC and were grown using standard methods in Dulbecco's Modified Eagle Medium supplemented with 10% fetal bovine serum, glutamine, penicillin (10,000 U/I) and streptomycin (10,000 U/I). Rat aortic smooth muscle cells (RASM) from Wistar rats were isolated by enzymatic dissociation using standard methods. The cells were positively identified as smooth muscle by indirect immunofluorescent staining for $\alpha$-actin, using mouse anti-$\alpha$-actin antibody and anti-mouse IgG FITC conjugate. RASM cells were grown in T-75 tissue culture flasks in 50% F12 nutrient medium and 50% Dulbecco's Modified Eagle Medium supplemented with 10% fetal bovine serum, glutamine, penicillin (10,000 U/I) and streptomycin (10,000 U/I). Cells were grown in 96-well plates for measure of nitrite production and cell viability. J774 macrophages were treated with endotoxin (10 $\mu$g/ml) for 24 hours; smooth muscle cells were treated with II-1 (100 U/ml) and gamma-interferon (50 U/ml) for 48 hours.

Concentration of nitrite, the degradation product of NO in the culture medium, was determined by mixing equal volumes of medium with the Griess reagent (1% sulfanilamide/0.1% naphtylethylenediamine dihydrochloride/2.5% $H_3PO_4$). The mixture was incubated for 10 minutes at room temperature to form the chromophore, then optical densities were determined at 550 nm. $NaNO_2$ was used as the standard. Spectrophotometric measurements were performed in a dual-wavelength spectrophotometer.

Mitochondrial respiration, an indicator of cell viability, was assessed by the mitochondrial-dependent reduction of MTT [3(4,5- dimethylthiazol-2-yl) - 2,5- diphenyltetrazolium bromide ] to formazan. Cells in 96-well plates were incubated (37° C.) with MTT (0.2 mg/ml for 60 minutes). Culture medium was removed by aspiration and the cells solubilized in DMS0 (100 μl). The extent of reduction of MTT to formazan within cells was quantitated by measurement of $OD_{550}$ using a microplate reader. Calibration curve for MTT-formazan was prepared in DMS0. MTT-formazan production by cells was expressed as a percentage of the values obtained from untreated cells.

Figure 2:
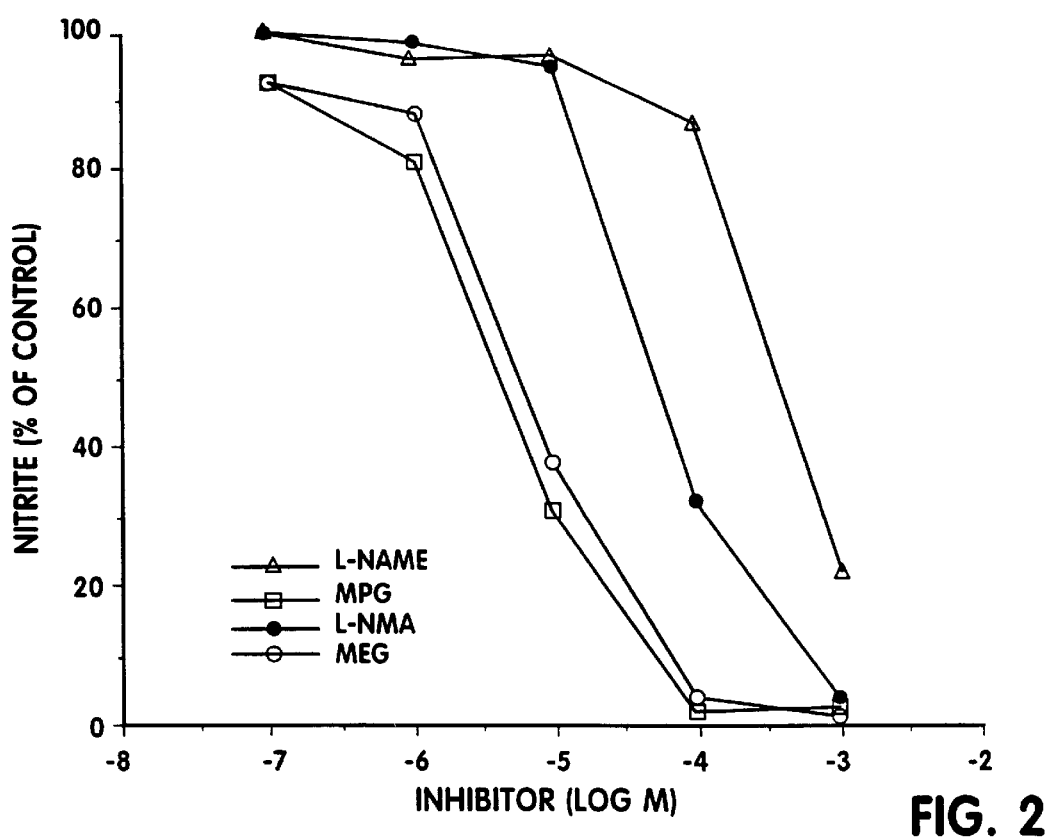
FIG. 2 is a graph of the effect of mercaptoethylguanidine (MEG), mercaptopropylguanidine (MPG), NG-methyl-L-arginine (L-NMA) and NG-nitro-L-arginine methyl ester (L-NAME) on nitrite production by immunostimulated vascular smooth muscle cells (N=3–6)
Figure 3:
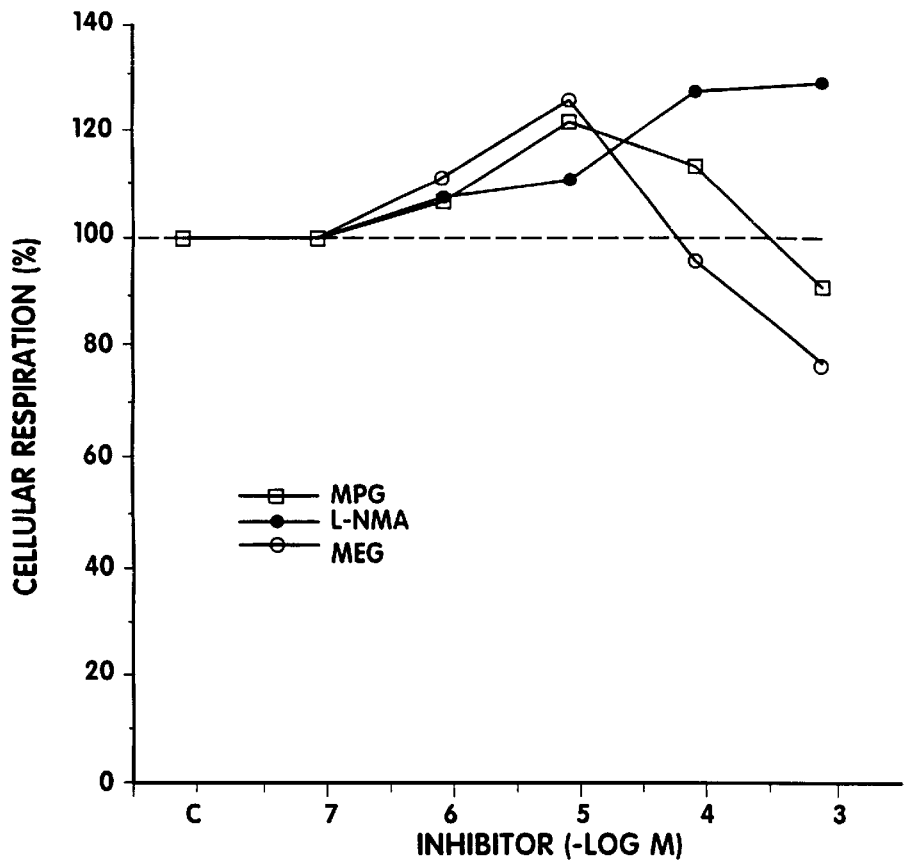
FIG. 3 is a graph of the effect of mercaptoethylguanidine (MEG), mercaptopropylguanidine (MPG), and NG-methyl-L-arginine (L-NMA) on cellular respiration by immunostimulated J774 macrophages (N=3–6) with "C" representing the activity in control samples, i.e., in the absence of any inhibitors.
Figure 4:
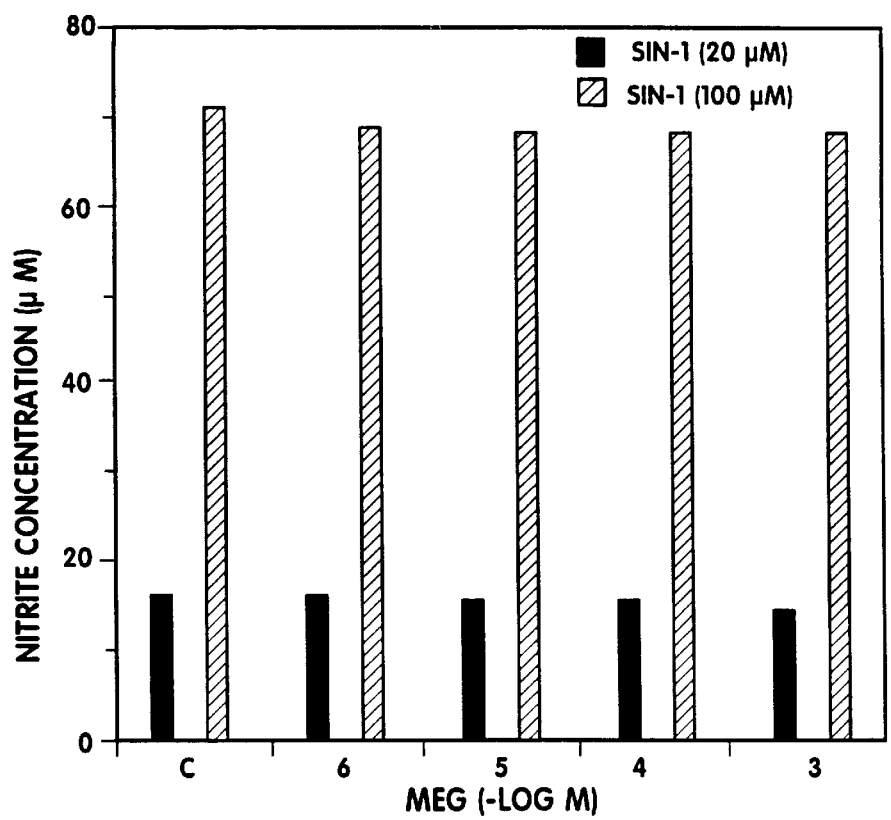
FIG. 4. is a graph of the effect of mercaptoethylguanidine (MEG) on nitrite production by the NO donor compound SIN-1 in culture medium containing 10% fetal calf serum (N=3) with "C" representing the activity in control samples, i.e., in the absence of any inhibitors.

Cells stimulated with endotoxin or with IL-1 and gamma-interferon produced nitric oxide, measured as an increase in nitrite concentration in the culture medium. This was dose-dependently inhibited by the mercapto derivatives, mercaptoethylguanidine (MEG) and mercaptopropylguanidine (MPG), which were substantially more potent inhibitors than the reference compounds NG-methyl-L-arginine (L-NMA) and NG-nitro-L-arginine methyl ester (L-NAME), as seen in FIGS. 1 and 2. The inhibition of nitrite production was not due to cell killing, as these agents in their effective doses (1–100 μM), did not decrease cellular viability (FIG. 3). At 1 mM, a slight reduction in viability was observed. Moreover, these agents did not scavenge nitrite or nitric oxide, as they did not interfere with the measured nitrite levels after incubation in the presence of the NO donor compound SIN-1 (FIG. 4).

EXAMPLE 2

This example illustrates the effect of selected mercapto derivatives on blood pressure in normal anesthetized rats. An increase in blood pressure by agents that inhibit NOS is a good measure of their inhibitory effect on the constitutive, endothelial NOS (ecNOS). Because L-NMA is known to be only weakly selective for inducible NOS (INOS), inhibiting iNOS and ecNOS to a substantially similar degree, L-NMA is useful as a reference compound in illustrating isoform selectivity. If a NOS-inhibiting agent increases blood pressure less strongly than L-NMA, (a generally non-selective compound), then the agent may be said to have selectivity for the inducible isoform.

In this particular example, Male Wistar rats were anesthetized with thiopentone sodium (120 mg/kg, i.p). The trachea was cannulated to facilitate respiration and the rectal temperature was maintained at 37° C. by means of a rectal probe connected to a homeothermic blanket. The right carotid artery was cannulated and connected to a pressure transducer for the measurement of phasic and mean arterial blood pressure and heart rate. The left and right femoral veins were cannulated for the administration of drugs.

Figure 5:
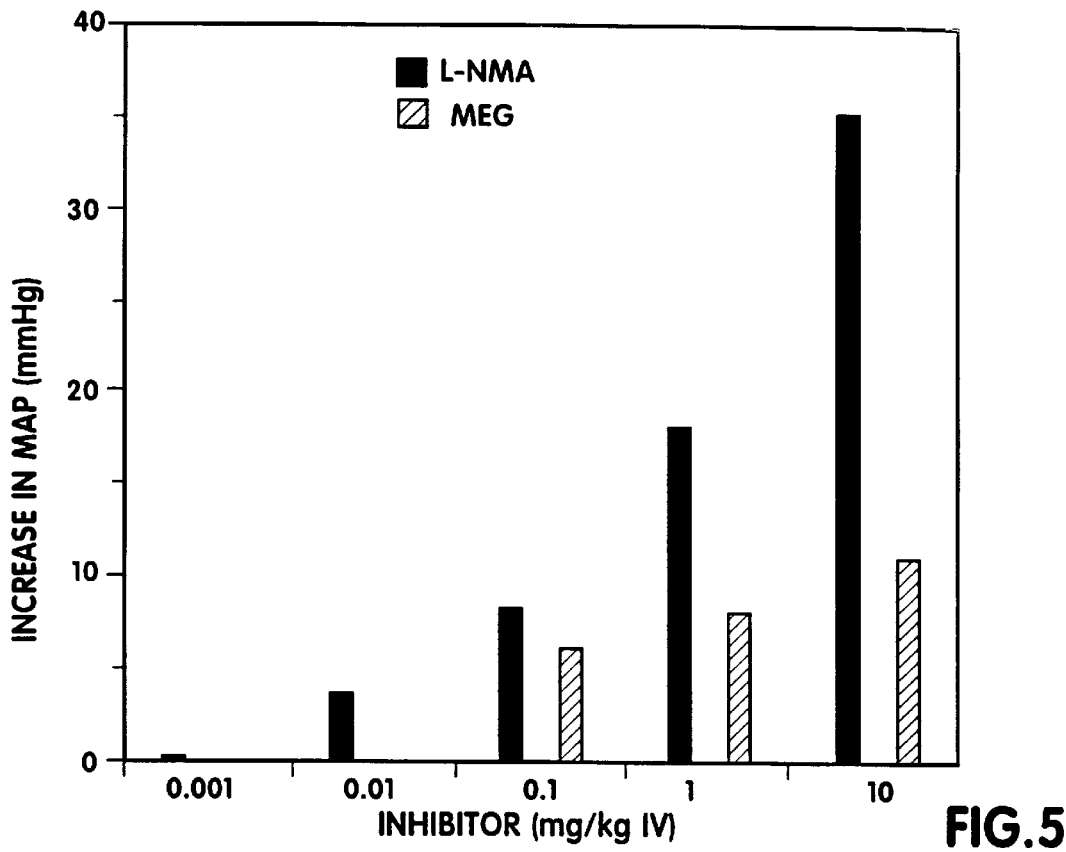
FIG. 5 is a graph of the effect of mercaptoethylguanidine (MEG) and NG-methyl-L-arginine (L-NMA) on mean arterial blood pressure (MAP) in anaesthetized rats (N=3–5)
Figure 6:
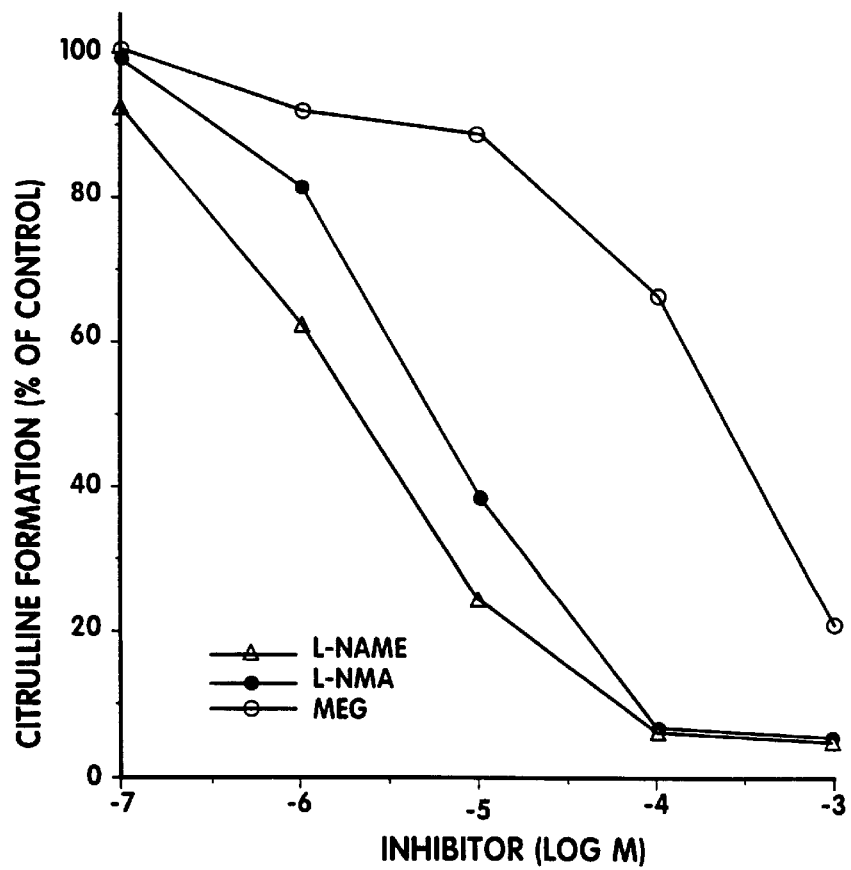
FIG. 6 is a graph of the effect of mercaptoethylguanidine (MEG), NG-methyl-L-arginine (L-NMA) and NG-nitro-L-arginine methyl ester (L-NAME) on citrulline formation by bovine aortae.

The mercapto derivatives MEG and MPG and reference compound L-NMA were administered in appropriate doses i.v. or i.p. to the animals. As shown in FIG. 5, mercapto derivatives caused only a slight increase in blood pressure, whereas the conventional reference compound L-NMA caused a pronounced and dosedependent pressor response, thereby illustrating the selectivity of the mercapto derivatives.

EXAMPLE 3

This is a further example of the relatively weak effect of mercaptoethylguanidine on ecNOS activity. ecNOS activity from bovine aorta was estimated as follows. The intimal surface of fresh bovine aortae was scraped in the presence of homogenation buffer composed of 50 mM Tris-HCI, 0.1 mM EDTA and 0.1 mMG EGT. Conversion of $[^3H]$-L-arginine to $[^3H]$-L-citrulline was measured in the homogenates as follows: cell homogenate (50 μl) was incubated in the presence of $[^3H]$-L-arginine (10 μM 5kBq/tube), NADPH (2 mM), calmodulin (30 nM), tetrahydrobiopterin (5 μM) and calcium (2 mM) for 20 minutes at 37° C. in HEPES buffer (pH 7.5). Reactions were stopped by dilution with 1 ml of ice cold HEPES buffer (pH 5.5) containing EGTA (2 mM) and EDTA (2 mM). Reaction mixtures were applied to Dowex 50W ($Na^+$ form) columns and the eluted $[^3H]$-L-citrulline activity was measured by scintillation counting. The dose dependent inhibition of ecNOS activity by mercaptoethylguanidine (MEG), when included in the incubation medium, was substantially less ($EC_{50}$=300 μM, n=3) than that of L-NMA ($EC_{50}$=20 μM, n=3) or L-NAME ($EC_{50}$=80 μM, n=3), thereby illustrating the isoform selectivity of the mercapto derivative.

EXAMPLE 4

This Example illustrates a method for synthesizing mercaptoethylguanidine sulphate. Mercaptoethylamine hydrochloride (2 g) was dissolved in methanol (5 ml) and cooled in a salt/ice bath. A cold solution of potassium hydroxide (0.99 g) in methanol (10 ml) was added and the mixture stirred. After 1 hour, the solution was filtered and S-methylisothiourea (2 g) was added to 12 ml of the filtrate. The solution was stirred at room temperature (18° C.) for 16 hours. The solution was then filtered and ether added to precipitate the crude product which was then recrystallized from an ether/ethanol mixture.

EXAMPLE 5

2-(Methylthio)ethylguanidine sulphate was prepared as follows: to a solution of 0.695 g S-methylisothiourea in 15 ml 90% methanol was added 0.456 g 2-(methylthio) ethylamine. The solution was stirred for 20 h at room temperature, filtered and the solvent removed in vacuo. The residue was crystallized from a mixture of methanol and ether.

EXAMPLE 6

2-(ethylthio)ethylguanidine sulphate was prepared using the procedure of example 5; however, 0.5 g of 2-(ethylthio) ethylamine was used instead of 2-(methylthio)ethylamine.

EXAMPLE 7

N-amidinylthiomorpholine sulphate was prepared as follows: thiomorpholine (3 ml) was added to a solution of 4.17 g S-methylisothiourea in 30 ml of 25% aqueous methanol and the solution was stirred overnight. The solvent was removed under reduced pressure and the residue taken up in warm methanol and filtered. The volume was reduced and the solution was left for 2 days after which the solid was collected.

EXAMPLE 8

N-amidinylthiazolidine sulphate was prepared as follows: thiazolidine (1g) was added to a solution of 1.56g S-methylisothiourea in 15 ml of 25% aqueous methanol and the solution was stirred overnight. The solvent was removed under reduced pressure and the residue recrystallized from methanol/water to give a white solid in low yield.

The detailed description of the invention presented above is provided by way of illustration, and it is not intended to limit the scope of the invention which is to be determined by the following claims.

What is claimed is:

1. A pharmacologically acceptable composition for inhibiting nitric oxide synthase in a mammal, comprising:

a mercapto derivative having the formula:

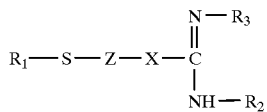

or a salt thereof, wherein $R_1$ is H, alkyl, alkenyl, phenyl, alkylene, alkenylene, or phenylalkylene or a substituted derivative thereof;

When $R_1$ is alkylene or alkenylene, $R_1$ optionally may be joined to either of the amidino Ns, to Z or to X of the above formula to form a 5-, 6- or 7- membered heterocyclic ring, with the proviso that when $R_1$ is attached to Z, Z is alkylene or alkenylene or a substituted derivative thereof, and, when $R_1$ is attached to X, X is either $CR_5$ or N;

$R_2$ and $R_3$ are independently H, lower alkyl, alkenyl, alkylene, alkenylene, amino, phenyl or phenylalkylene, or a substituted derivative thereof;

When $R_2$ is alkylene or alkenylene, $R_2$ optionally may be joined to the imino N of the above formula to form a 5- or 6- membered heterocyclic ring;

Z is an alkylene, alkenylene, cycloalkylene or cycloalkenylene, or a substituted derivative thereof;

When $R_2$ or $R_3$ is alkylene or alkenylene, $R_2$ or $R_3$ optionally may be joined to Z to form a 5- or 6- membered heterocyclic ring including N, C and not more than one atom of O or S, with the proviso that said heterocyclic ring optionally being substituted with a lower alkyl, alkoxy, halogen, hydroxy or amino;

X is N, $NR_4$, O, $CR_5$ or $CR_4 R_5$;

$R_4$ is independently H, alkyl, thioalkylene or thioesteralkylene;

$R_5$ is independently H, alkyl, alkylene, alkenylene, alkylene, alkenylene, thioalkylene, thioesteralkylene, amino or carboxyl;

When $R_4$ is alkylene, alkenylene, thioalkylene, or thioesteralkylene, $R_4$ optionally may be joined to $R_2$ or $R_3$ to form a 5- or 6- membered heterocyclic ring including N, C and not more than one atom of O or S, with the proviso that $R_2$ or $R_3$ is alkylene, alkenylene, amino, phenyl, phenylalkylene, or a substituted derivative thereof wherein the substituted derivative is lower alkyl or halogen; and a pharmaceutically acceptable carrier, said mercapto derivative present in said composition in an effective amount to inhibit nitric oxide synthase in said mammal.

2. A pharmacologically acceptable composition for inhibiting nitric oxide synthase in a mammal, comprising:

a mercapto derivative having the formula:

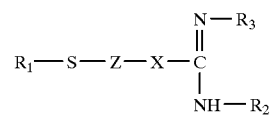

or a salt thereof, wherein $R_1$ is H, alkyl, alkenyl, phenyl, alkylene, alkenylene, or phenylalkylene or a substituted derivative thereof;

When $R_1$ is alkylene or alkenylene, $R_1$ optionally may be joined to Z or to X of the above formula to form a 5-membered heterocyclic ring, with the proviso that when $R_1$ is attached to Z, Z is alkylene or alkenylene or a substituted derivative thereof, and, when $R_1$ is attached to X, X is either $CR_5$ or N;

$R_2$ and $R_3$ are independently H, lower alkyl, alkenyl, alkylene, alkenylene, amino, phenyl or phenylalkylene, or a substituted derivative thereof;

When $R_2$ is alkylene or alkenylene, $R_2$ optionally may be joined to the imino N of the above formula to form a 5- or 6- membered heterocyclic ring;

Z is an alkylene, alkenylene, cycloalkylene or cycloalkenylene, or a substituted derivative thereof;

When $R_2$ or $R_3$ is alkylene or alkenylene, $R_2$ or $R_3$ optionally may be joined to Z to form a 5- or 6- membered heterocyclic ring including N, C and not more than one atom of O or S, wiht the proviso that said heterocyclic ring optionally being substituted with a lower alkyl, alkoxy, halogen, hydroxy or amino;

X is N, $NR_4$, O, $CR_5$ or $CR_4 R_5$;

$R_4$ is independently H, alkyl, thioalkylene or thioesteralkylene;

$R_5$ is independently H, alkyl, alkylene, alkenylene, alkylene, alkenylene, thioalkylene, thioesteralkylene, amino or carboxyl;

When $R_4$ is alkylene, alkenylene, thioalkylene, or thioesteralkylene, $R_4$ optionally may be joined to $R_2$ or $R_3$ to form 5- or 6- membered heterocyclic ring including $N_1$ C and not more than one atom of O or S, with the proviso that $R_2$ or $R_3$ is alkylene, alkenylene, amino, phenyl, phenylalkylene, or a substituted derivative thereof wherein the substituted derivative is lower alkyl or halogen; and a pharmaceutically acceptable carrier, said mercapto derivative present in said composition in an effective amount to inhibit nitric oxide synthase in said mammal.

3. The composition of claim 1 wherein said substituted derivative of $R_1$ is selected from the group consisting of one or more of alkoxy, halogen, hydroxy, amino and nitro.

4. The composition of claim 1 wherein said substituted derivative of $R_2$ or $R_3$ is selected from the group consisting of lower alkyl and halogen.

5. The composition of claim 1 wherein said $R_4$ or $R_5$ thioalkylene has a formula [—$(CH_2)_n$—SH] and n is 1 to 4.

6. The composition of claim 1 wherein said $R_4$ or $R_5$ thioesteralkylene has a formula [—$(CH_2)_n$—S—$R_6$] where $R_6$ is a lower alkyl and n is 1 to 4.

7. The composition of claim 1 wherein said substituted derivative of Z is selected from the group consisting of alkoxy, halogen, hydroxy, amino and nitro.

8. The composition of claim 1 wherein $R_1$ is selected from the group consisting of H and lower alkyl, $R_2$ is H, $R_3$ is H, X is $NR_4$, $R_4$ is selected from the group consisting of H, methyl and ethyl, and Z is alkylene.

9. The composition of claim 1 wherein $R_1$ is H, $R_2$ is H, $R_3$ is H, X is $NR_4$, $R_4$ is H and Z is a $C_{1-6}$ alkylene.

10. The composition of claim 1 wherein said mercapto derivative is selected from the group consisting of mercaptoethylguanidine, mercaptopropylguanidine, S-methylmercaptoethylguanidine and S-methylmercaptopropylguanidine.

11. The composition of claim 1 formulated for oral, rectal, nasal, topical, buccal, sub-lingual, vaginal, parenteral, intramuscular, sub-cutaneous, intravenous, inhalation or insufflation administration.

12. The composition of claim 1 formulated for oral administration, said carrier including an ingredient selected from the group consisting of a binding agent, filler, lubricant, disintegrant, wetting agent, inert diluent, surface active agent, dispersing agent, suspending agent, emulsifying agent, edible oil, flavoring agent and mixtures thereof.

13. The composition of claim 1 formulated for topical administration in the mouth, said carrier including an ingredient selected from the group consisting of a flavor, sucrose, acacia, tragacanth, gelatin, glycerin and mixtures thereof.

14. The composition of claim 1 formulated for nasal administration, said carrier including an ingredient selected from the group consisting of a dispersing agent, solubilizing agent, suspending agent and mixtures thereof.

15. The composition of claim 1 formulated for administration by inhalation, said carrier including a propellant.

16. The composition of claim 15 wherein said propellant is selected from the group consisting of dichlorodifluoromethane, trichlorofluoromethane, dichlorotetrafluoroethane, carbon dioxide and and mixtures thereof.

17. The composition of claim 1 formulated for administration by inhalation or insufflation, said carrier including an ingredient selected from the group consisting of lactose, starch and mixtures thereof.

18. The composition of claim 1 formulated for parenteral administration, said carrier including an ingredient selected from the group consisting of an anti-oxidant, buffer, bacteriostat, suspending agent, thickening agent, saline, water and mixtures thereof.

19. The composition of claim 1 formulated for rectal administration, said carrier including an ingredient selected from the group consisting of cocoa butter, polyethylene glycol and mixtures thereof.

20. The composition of claim 1 formulated to include an ingredient selected from the group consisting of an antimicrobial agent, an immunosuppressant, a preservative and mixtures thereof.

21. The composition of claim 1 formulated for administration at a dose of from about 5 mg to about 17.5 g/day of said mercapto derivative.

22. The composition of claim 21 formulated for administration at a dose of from about 5 mg to about 10 g/day of said mercapto derivative.

23. The composition of claim 22 formulated for administration at a dose of from about 100 mg to about 3 g/day of said mercapto derivative.

* * * * *